United States Patent [19]

Belmont et al.

[11] Patent Number: 5,268,483

[45] Date of Patent: Dec. 7, 1993

[54] PROCESS FOR THE PREPARATION OF AN L-ALANINE COMPOUND

[75] Inventors: Daniel T. Belmont, Holland; Valerie Hendrickson, Grandville; Mark J. Hoekman, Holland, all of Mich.

[73] Assignee: Warner-Lambert Company, Morris Plains, N.J.

[21] Appl. No.: 29,647

[22] Filed: Mar. 11, 1993

Related U.S. Application Data

[62] Division of Ser. No. 748,148, Aug. 21, 1991, Pat. No. 5,220,031, which is a division of Ser. No. 690,012, Apr. 23, 1991, Pat. No. 5,089,616.

[51] Int. Cl.$^5$ .............................................. C07D 277/40
[52] U.S. Cl. .................................................... 548/194
[58] Field of Search .......................................... 548/194

[56] References Cited

U.S. PATENT DOCUMENTS 2,556,907 6/1951 Emmick ............................... 562/562
2,657,230 10/1953 Rogers ................................. 562/562

OTHER PUBLICATIONS

Elrel "Stereochemistry of Chemistry Compounds" pp. 49–55 (1962).
Fogassy et al. "Tetrahedron Letters" vol. 21 (1980) pp. 647–650.

Primary Examiner—Robert W. Ramsuer
Attorney, Agent, or Firm—Francis J. Tinney

[57] ABSTRACT

An improved process for the preparation of [1S-(1R*,2S*,3R*)]-N (4-morpholinylsulfonyl)-L-phenylalanyl-3-(2-amino-4 thiazolyl)-N-[(1-cyclohexylmethyl) -2,3-dihydroxy-5-methylhexyl]-L-alaninamide is described where the key intermediate, 3-(2-amino 4-thiazolyl)-L-alanine is converted without protecting the aminothiazole group to the desired compound, as well as valuable intermediates used in the process.

6 Claims, No Drawings

PROCESS FOR THE PREPARATION OF AN L-ALANINE COMPOUND

This is a divisional application U.S. Ser. No. 07/748,148 filed Aug. 21, 1991, now U.S. Pat. No. 5,220,031, which is a divisional application of U.S. Ser. No. 07/690,012, filed Apr. 23, 1991, which application is now U.S. Pat. No. 5,089,616.

BACKGROUND OF THE INVENTION

European Published Patent Application 0399556, which is herein incorporated by reference, discloses a novel series of amino-substituted heterocycles.

The compounds disclosed in European Published Patent Application 0399556 are useful for treating renin-associated hypertension, congestive heart failure, glaucoma, hyperaldosteronism, diseases caused by retroviruses including HTLV I, II, and III, as well as the use of the compounds as diagnostic tools for determining the presence of renin-associated hypertension or hyperaldosteronism. Particularly valuable in the aforementioned therapeutic categories and in particular in the treatment of renin-associated hypertension is [1S-(1R*,2S*,3R*)]-N-(4-morpholinylsulfonyl)-L-phenylalanyl-3-(2-amino-4-thiazolyl)-N-[1-(cyclohexylmethyl)-2,3-dihydroxy-5-methylhexyl]-L-alaninamide. The aforementioned compound has been prepared by a procedure utilizing 3-(2-amino-4-thiazolyl)-L-alanine as a key intermediate. The amino group on the thiazole ring of this intermediate was protected to prevent byproducts resulting from coupling through the aminothiazole group. Additionally, the process requires an expensive starting material, uses potentially hazardous reagents and intermediates, and finally involves the use of chromatography for purification of intermediates and final product.

The object of the present invention is an improved process for preparing the compound described above by using a novel synthesis.

Further, we have unexpectedly found that the key intermediate, 3-(2-amino-4-thiazolyl)-L-alanine can be used in the present procedure without protecting the aninothiazole group. Thus, the present method eliminates two steps required for protection and removal of the blocking group on the aminothiazole group. Moreover, the present method proceeds from an inexpensive starting material, uses nonhazardous reagents and finally does not require chromatography to purify intermediates and final product. Therefore, the present process is amenable to large-scale synthesis.

SUMMARY OF THE INVENTION

Accordingly, a first aspect of the present invention is an improved process for the preparation of the compound of Formula I

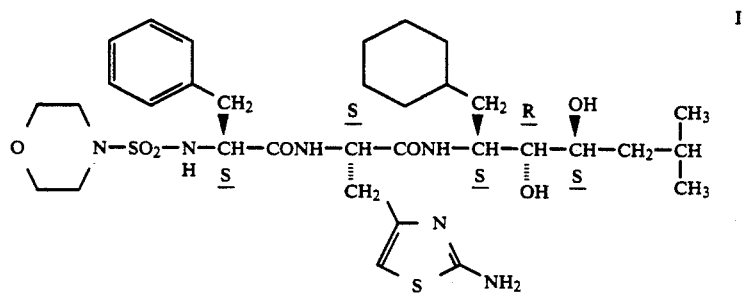

and pharmaceutically acceptable acid addition salts thereof which comprises:

Step (a) treating the racemic compound of Formula VIII

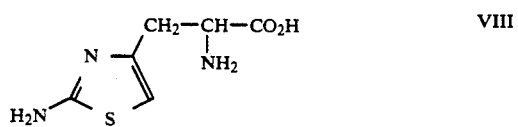

with L-glutamic acid in a solvent to afford the compound of Formula VII;

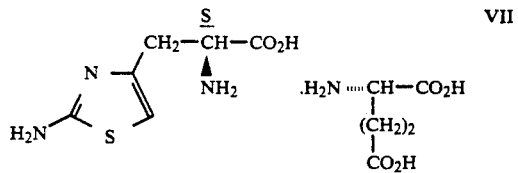

Step (b) treating the compound of Formula VII with a base in solvent to afford the compound of Formula VIIIa;

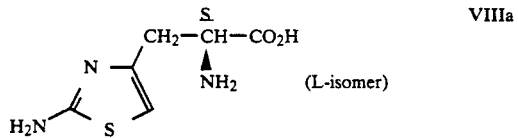

Step (c) treating the compound of Formula VIIIa with a compound of Formula

R—OH wherein R is alkyl or benzyl in the presence of an acid to afford the compound of Formula VI wherein R is as defined above;

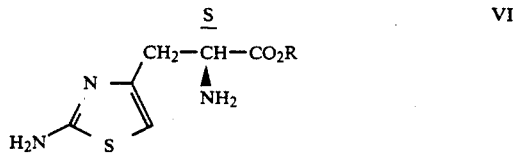

Step (d) treating the compound of Formula VI with the compound of Formula V

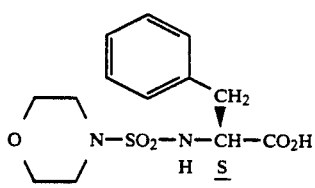

in the presence of a coupling reagent and a solvent to afford the compound of Formula IV wherein R is as defined above;

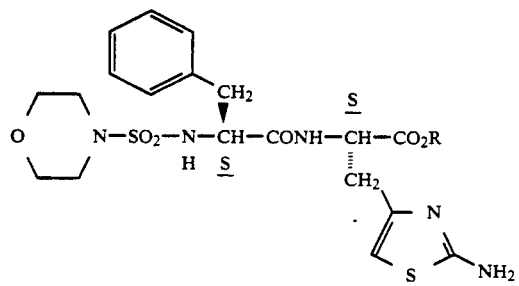

Step (e) treating the compound of Formula IV with a base in a solvent to afford the compound of Formula III;

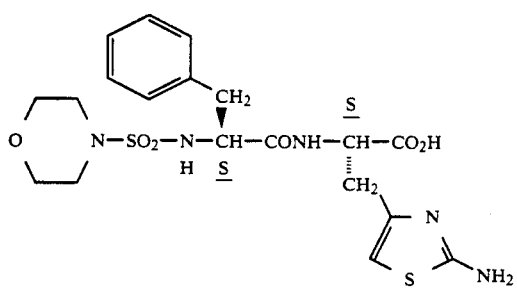

Step (f) treating the compound of Formula III with the compound of Formula II

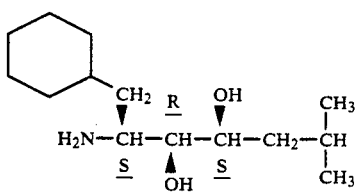

in the presence of a coupling reagent and a solvent to afford the compound of Formula I;

Step (g) and, if desired, converting the resulting compound of Formula I to a corresponding pharmaceutically acceptable acid addition salt by conventional means, and if so desired, converting the corresponding pharmaceutically acceptable acid addition salt to a compound of Formula I by conventional means.

A second aspect of the present invention is an improved process for the preparation of the compound of Formula VIIIa

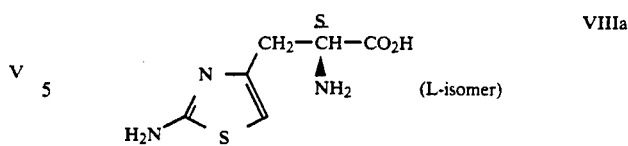

and pharmaceutically acceptable salts thereof comprises:

Step (a) treating the racemic compound of Formula VIII

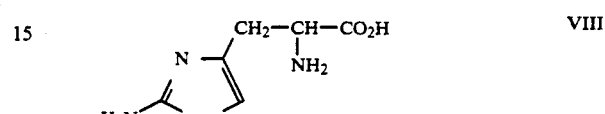

with L-glutamic acid in a solvent to afford the compound of Formula VII;

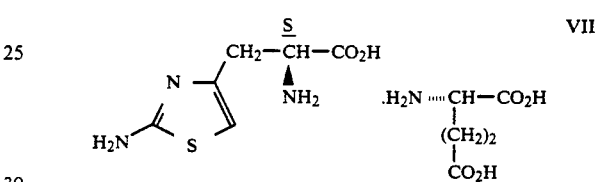

Step (b) treating the compound of Formula VII with a base in a solvent to afford the compound of Formula VIIIa;

Step (c) and, if desired, converting the resulting compound of Formula VIIIa to a corresponding pharmaceutically acceptable salt by conventional means, and if so desired, converting the corresponding pharmaceutically acceptable salt to a compound of Formula VIIIa by conventional means.

A third aspect of the present invention is a novel intermediate of Formula VII

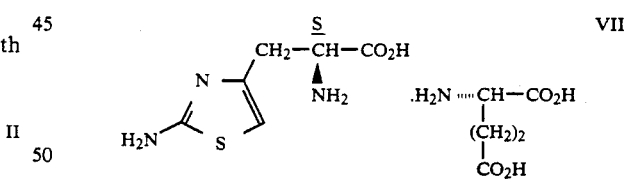

which is useful in the preparation of the compound of Formula VIIIa which in turn is useful in the preparation of the compound of Formula I.

A fourth aspect of the present invention is a novel intermediate of Formula VIIIa

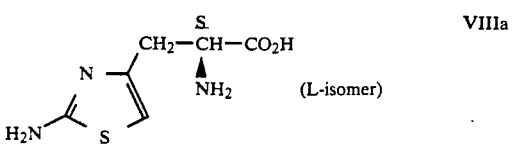

and pharmaceutically acceptable salts thereof which is useful in the preparation of the compound of Formula VIIIa.

DETAILED DESCRIPTION OF THE INVENTION

In this invention, the term "alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The compound of Formula I is capable of further forming pharmaceutically acceptable acid addition salts and the compound of Formula VIIIa is capable of forming both pharmaceutically acceptable acid addition and/or base salts. All of these forms are within the scope of the present invention.

Pharmaceutically acceptable acid addition salts of the compound of Formula I and Formula VIIIa include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Bergs S. M., et al, "Pharmaceutical Salts," Journal of Pharmaceutical Science, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or amines such as alkali and alkaline earth metals or organic amines. Examples of metals used as cations are sodium, potassium, magnesium, calcium and the like. Examples of suitable amines are N,N,-dibenzylethylenediamine, chloroprocaine, choline, diethanolamine, ethylenediamine, N-methylglucamine, and procaine (see, for example, Berge S. M., et al, Journal of Pharmaceutical Science, Vol. 66, pages 1-19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

As previously described, the compound of Formula I is useful for the treatment of renin-associated hypertension, congestive heart failure, glaucoma, hyperaldosteronism, diseases caused by retroviruses including HTLV I, II, and III, as well as the use of the compound as a diagnostic tool for determining the presence of renin-associated hypertension or hyperaldosteronism.

The process of the present invention in its first aspect is a new, improved, economical, and commercially feasible method for preparing the compound of Formula I. Furthermore, the process can be carried out without protecting the amino group attached to the thiazole ring of the key intermediate, 3-(2-amino-4-thiazolyl)-L-alanine. The process of the present invention in its first aspect is outlined in Scheme I.

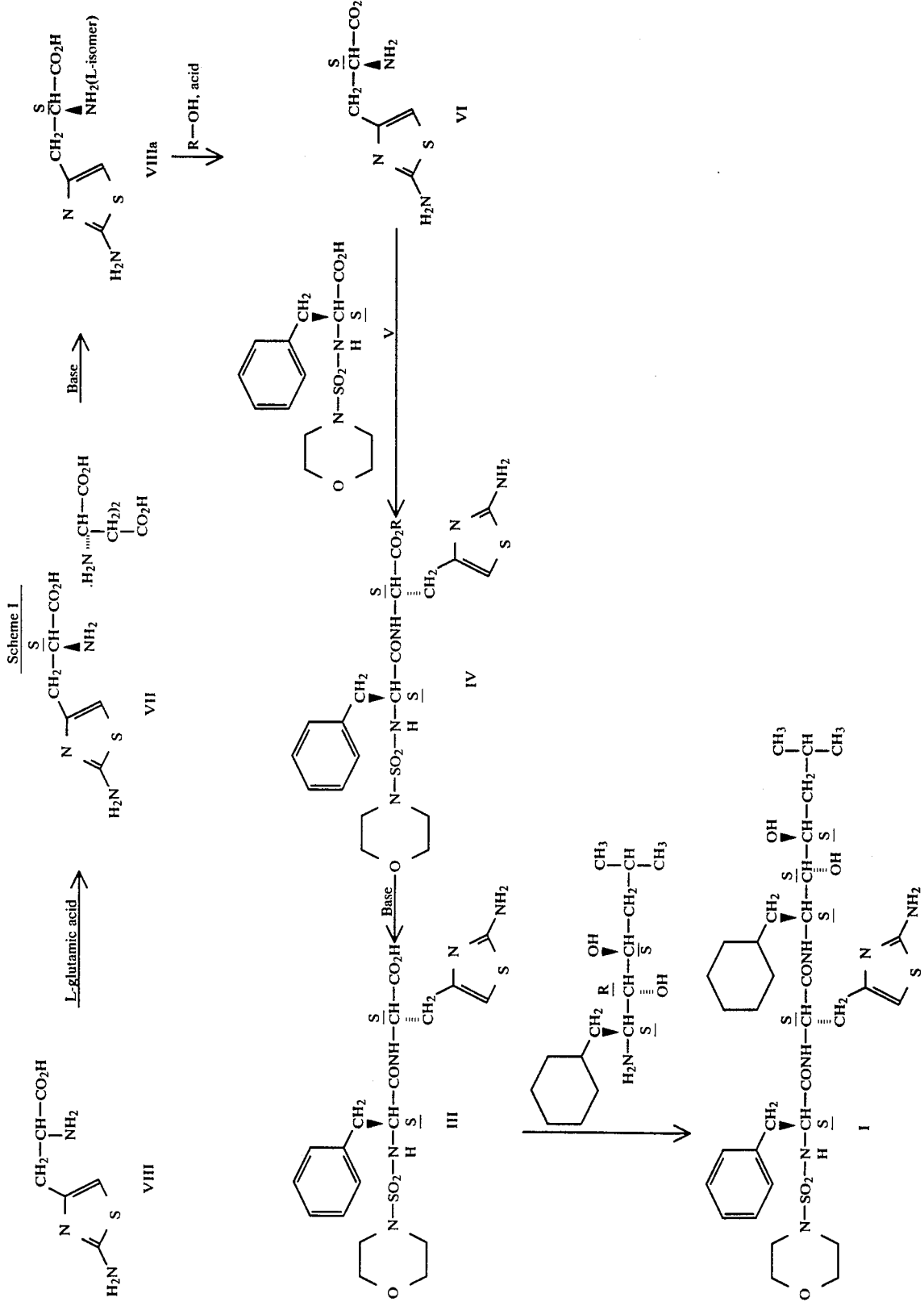

Thus, the compound of Formula VIII which is a racemic mixture of isomers is treated with L-glutamic acid in a solvent such as, for example, methanol water and the like at about room temperature to about 70° C. to afford a mixture of diastereomeric salts from which the desired LL diastereomeric salt of Formula VII is obtained by crystallization from an alcohol such as, for example, methanol and the like. Preferably the reaction is carried out in methanol-water at about 54° C. with subsequent crystallization from methanol-water (50:50). The salt of Formula VII is treated with a base such as, for example, triethylamine, pyridine, morpholine and the like in a solvent such as, for example, an alcohol such as methanol and the like at about the reflux temperature of the solvent for about 1 hour followed by cooling to about 5° C. to afford the compound of Formula VIIIa as the enantiomerically pure L-isomer. Preferably the reaction is carried out with triethylamine in methanol at about reflux for about 1 hour followed by cooling to about 5° C. The amino acid of Formula VIIIa is treated with a compound of formula

wherein R is alkyl or benzyl in the presence of an acid such as, for example, hydrochloric acid, hydrobromic acid, sulfuric acid, para-toluenesulfonic acid, methanesulfonic acid, and the like at about 0° C. to about reflux for about 1 hour to about 24 hours to afford the ester of Formula VI wherein R is as defined above. Preferably the reaction is carried out with a saturated hydrogen chloride solution of the compound of formula R—OH at about 24° C. for about 6 hours followed by heating to about reflux and then cooling to about 5° C. for about 1 hour. The compound of Formula VI is reacted with the compound of Formula V in the presence of a coupling reagent such as, for example, dicyclohexylcarbodiimide and hydroxybenzotriazole, carbonyldiimidazole, a mixed anhydride, for example, isobutyl chloroformate in the presence of a base such as, for example, triethylamine, n-methylmorpholine and the like and a solvent such as, for example, ethyl acetate, dimethylformamide, tetrahydrofuran, dichloromethane, mixtures thereof such as, for example, dimethylformamide-ethyl acetate and the like at about 0° C. to about room temperature for about 30 minutes to about 24 hours to afford the compound of Formula IV wherein R is as defined above. Preferably the reaction is carried out with dicyclohexylcarbodiimide and hydroxybenzotriazole in ethyl acetate at about 5° C. for about 15 minutes followed by reaction at about room temperature for about 15 hours. Optionally, the compound of Formula IV may be isolated as a salt by treatment with an acid such as, for example, hydrochloric acid, hydrobromic acid, sulfuric acid and the like in an alcohol such as, for example, methanol, ethanol, isopropanol and the like. Preferably the monohydrochloride salt of the compound of Formula IV is obtained by treatment of the compound of Formula IV with hydrogen chloride in isopropanol. The salt of a compound of Formula IV is treated with a base such as, for example, an alkali metal hydroxide, an alkaline earth metal hydroxide such as sodium hydroxide, potassium hydroxide, calcium hydroxide and the like in a solvent such as, for example, methanol-water, dioxane-water, acetone water, tetrahydrofuran-water and the like at about 0° C. to about room temperature for about 30 minutes to about 12 hours to afford the compound of Formula III. Preferably the reaction is carried out with sodium hydroxide in tetrahydrofuran-hydrobromic water at about 0° C. to about 5° C. for about 3 hours. The compound of Formula III is reacted with the compound of Formula II in the presence of a coupling reagent and a solvent using the methodology used to prepare a compound of Formula IV from a compound of Formula VI and a compound of Formula V.

The compound of Formula VIII may be prepared by the methodology described by Silberg, A., et al, *Chemische Berichte*, Vol. 97, pages 1767-69 (1964). Patt, W. C., et al, *Synthetic Communications*, Vol. 20, pages 3097-3102 (1990) described an asymmetric synthesis of α-N-BOC-β-(2'-amino-4'-thiazolyl)alanine benzyl ester which is a protected derivative of 3-(2-amino-4-thiazolyl)-L-alanine. However, unlike the present procedure, this method uses the expensive N-BOC-aspartic-α-benzyl ester as the starting material and employs diazomethane, a potentially hazardous reagent.

The following nonlimiting example illustrates the inventors' preferred method for preparing the compound and valuable intermediates of the present invention.

EXAMPLE 1

[1S-(1R*,2S*,3R*)]-N-(4-Morpholinylsulfonyl)-L-phenylalanyl-3-(2-amino-4-thiazolyl)-N-[1-cyclohexylmethyl)-2,3-dihydroxy-5-methylhexyl]-L-alaninamid Step A: Preparation of
3-(2-Amino-4-thiazolyl)-L-alanine-L-glutamic acid salt DL-3-(2-Amino-4-thiazolyl)alanine, 41.8 kg (223 mol) (Silberg, A., et al, *Chemische Berichte*, Vol. 97, pages 1767-69 (1964)) and 26.3 kg (179 mol) of L-glutamic acid are dissolved in 620 L of water at 60° C. Methanol (620 L) is added to the solution and the solution is cooled to 25° C. to crystallize the salt. After stirring for 2 to 3 hours at 25° C., the product is filtered and washed with 40 L of methanol. The product is dried at 40° C. under vacuum to give 37.6 kg of 3-(2-amino-4-thiazolyl)-L-alanine L-glutamic acid salt as a white solid. Infrared spectrum (IR) (mineral oil): 2927 (s, br), 1643 (s), 1605 (s), 1548 (s), 1407 (sh) cm$^{-1}$.

Step B: Preparation of
3-(2-Amino-4-thiazolyl)-L-alanine 3-(2-Amino-4-thiazolyl)-L-alanine L-glutamic acid salt, 37.6 kg (112 mol) and 420 L of methanol are charged into a reactor and stirred as 34.4 kg of triethylamine is added. The slurry is heated to reflux for 1 hour and then cooled to 5° C. The product is filtered, washed with 25 L of methanol to give 26.3 kg of 3-(2 amino-4-thiazolyl)-L-alanine as a white solid containing methanol. A dried sample is >99% pure and >99% enantiomeric excess by chiral high pressure liquid chromatography (HPLC); IR (mineral oil): 3170 (s, br), 1618 (s), 1525 (s), 1108 (m) cm$^{-1}$.

Step C: Preparation of
3-(2-Amino-4-thiazolyl)-L-alanine methyl ester dihydrochloride 3-(2-Amino-4-thiazolyl)-L alanine containing methanol, 26.3 kg (76 mol) and 72 L of methanol are charged into a reactor and stirred at 5° C., followed by 16.9 kg of anhydrous hydrogen chloride gas and stirred at 25° C. for 5 hours. The solution is heated to reflux and then cooled to 5° C. and held for 1 hour. The product is filtered and dried under vacuum at 50° C. to give 17.7 kg of 3-(2-amino-4-thiazolyl)-L-alanine methyl ester dihydrochloride as an off-white solid, 99% pure by HPLC; IR (mineral oil): 3410 (sh), 1749 (sh), 1631 (sh), 1225 (m) cm$^{-1}$.

Step D: Preparation of N-(4-Morpholinylsulfonyl)-L-phenylalanyl-3-(2-amino-4-thiazolyl)-L-alanine methyl ester monohydrochloride 3-(2-Amino-4-thiazolyl)-L-alanine methyl ester dihydrochloride, 12 kg (43.8 mol), 13.8 kg of N-(4-morpholinylsulfonyl)-L-phenylalanine (European Published Patent Application 0399556), 6.0 kg of hydroxybenzotriazole (HOBT), and 110 L of dimethylformamide are charged into a 800 L reactor and cooled to 5° C. Triethylamine, 9.4 kg, is charged over 10 minutes and cooled to 5° C. A solution of 9.5 kg of dicyclohexylcarbodiimide in 350 L of ethyl acetate is charged into the reaction mixture over a 15 minute period at 5° C. The slurry is allowed to warm to room temperature and stirred overnight. The slurry is diluted with 424 L of ethyl acetate and filtered. The cake is washed with 50 L of ethyl acetate. The filtrate is washed with water (2×140 L) and saturated sodium bicarbonate solution (2×150 L). The solution is diluted with 193 L of isopropyl alcohol. After cooling to 5° C., anhydrous hydrogen chloride gas (3.2 kg) is added to precipitate the product. After isolation by filtration, the product is dried at 25° C. under vacuum to give 18 kg of N-(4-morpholinyl-sulfonyl)-L-phenylalanyl 3-(2-amino-4-thiazolyl)-L-alanine methyl ester monohydrochloride as a white solid, 99.6% pure by HPLC; mass spectrum (chemical ionization) 498 M+H.

Step E: Preparation of N-(4-Morpholinylsulfonyl)-L-phenylalanyl-3-(2-amino-4-thiazolyl)-L-alanine N-(4-Morpholinylsulfonyl)-L-phenylalanyl-3-(2-amino-4-thiazolyl)-L-alanine methyl ester monohydrochloride, 2057.6 g, and 6 L of tetrahydrofuran are charged into a 50 L reactor and stirred to a thick slurry at 0° to 5° C. A solution of 456 g of sodium hydroxide in 11.4 L of water is added over 2 hours at 0° to 5° C. After stirring the reaction mixture for 30 minutes, a solution of 630.8 mL of concentrated hydrochloric acid in 7.6 L of water is added over 2 hours at 0° to 5° C. The product precipitates as a thick slurry, which is filtered and the cake washed with water (2×500 mL). The solid is dried under vacuum at 40° C. to give 1700 g of N-(4-morpholinylsulfonyl)-L-phenylalanyl-3-(2-amino-4-thiazolyl)-L-alanine as a white solid, 99.5% pure. A second crop of 108 g is obtained of 99.7% purity by HPLC; mp 149°-151° C.

Step F: Preparation of 1S-(1R*,2S*,3R*)]-N-(4-morpholinylsulfonyl)-L-phenylalanyl-3-(2-amino-4-thiazolyl)-N-[(1-cyclohexylmethyl)-2,3-dihydroxy-5-methylhexyl]-L-alaninamide 1-N-Hydroxybenzotriazole, 190.6 g, 395.0 g of [2S (2R*,3S*,4R*)]-2-amino-1-cyclohexyl-6-methyl-3,4-heptanediol (U.S. Pat. No. 4,680,284 and 4,845,079), 682.4 g (1.62 mol) of N-(4-morpholinyl-sulfonyl)-L-phenylalanyl-3-(2-amino-4-thiazolyl)-L-alanine and 20 L of ethyl acetate are charged into a 50 L reactor and the slurry is stirred. Triethylamine, 107.1 g with 0.5 L of ethyl acetate, is added to the mixture and stirred for 1 hour at 30° C. A solution of 300.0 g of dicyclohexylcarbodiimide dissolved in 2.5 L of ethyl acetate is added to the reaction mixture over 15 to 30 minutes. The slurry is warmed to 35° to 40° C. and stirred at that temperature for 48 hours, cooled to 25° C., and the solids removed by filtration. The filtrate is washed with 0.5N aqueous hydrochloric acid solution (4 L), saturated sodium bicarbonate solution (4×4 L), and water (2 L). The solution is concentrated to a thick slurry under vacuum, chilled to 5° C., and the crude product solid collected by filtration and dried under vacuum at 40° C. The crude product and 4 L of isopropanol are charged into a 12 L reactor and the slurry is heated to 45° C. Water, 1 L, is added and heating continued to 60° C. The solution is cooled slowly to crystallize the product and then chilled to 10° C. The slurry is filtered and the cake is washed with cold isopropanol. After drying at 40° C. under vacuum, 770 g of [1S-(1R*,2S*,3R*)]-N-(4-morpholinylsulfonyl)-L-phenylalanyl-3-(2-amino-4-thiazolyl)-N-[(1-cyclohexylmethyl)-2,3-dihydroxy-5-methylhexyl]-L-alaninamide is obtained as white needles of >99% purity by HPLC; mass spectrum (fast atom bombardment): 709.2 M+.

We claim:

1. A process for the preparation of the compound of Formula VIIIa

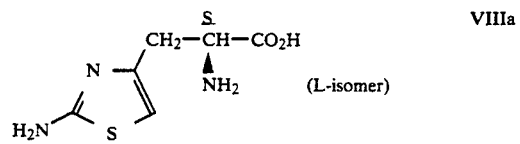

and pharmaceutically acceptable salts thereof comprises:

Step (a) treating the racemic compound of Formula VIII

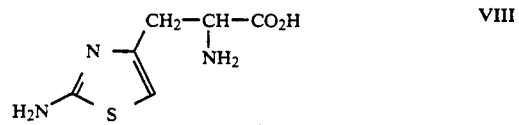

with L-glutamic acid in a solvent to afford the compound of Formula VII;

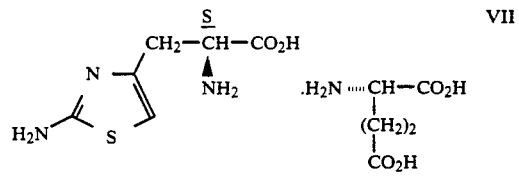

Step (b) treating the compound of Formula VII with a base in a solvent to afford the compound of Formula VIIIa;

Step (c) and, if desired, converting the resulting compound of Formula VIIIa to a corresponding pharmaceutically acceptable salt by conventional means.

2. A process according to claim 1 wherein the solvent in Step (a) is methanol-water.

3. A process according to claim 1 wherein the base in Step (b) is selected from the group consisting of triethylamine, pyridine, and morpholine.

4. A process according to claim 3 wherein the base is triethylamine.

5. A process according to claim 1 wherein the solvent in Step (b) is selected from the group consisting of methanol and ethanol.

6. A process according to claim 5 wherein the solvent is methanol.

* * * * *